United States Patent
Hung et al.

(10) Patent No.: US 10,188,850 B2
(45) Date of Patent: Jan. 29, 2019

(54) FLUID LEVEL MONITORING DEVICE

(71) Applicant: FIVAMED INC., Halifax (CA)

(72) Inventors: Orlando Hung, Halifax (CA); Gleb Sekretta, Halifax (CA); Benjamin Garvey, Halifax (CA); Lee Babin, Halifax (CA); Alistair Trower, Halifax (CA)

(73) Assignee: FIVAMED INC., Halifax (CA)

( * ) Notice: Subject to any disclaimer, the term of this patent is extended or adjusted under 35 U.S.C. 154(b) by 138 days.

(21) Appl. No.: 15/114,378

(22) PCT Filed: Jan. 26, 2015

(86) PCT No.: PCT/IB2015/001034
§ 371 (c)(1),
(2) Date: Jul. 26, 2016

(87) PCT Pub. No.: WO2015/132676
PCT Pub. Date: Sep. 11, 2015

(65) Prior Publication Data
US 2016/0339229 A1  Nov. 24, 2016

Related U.S. Application Data

(60) Provisional application No. 61/932,144, filed on Jan. 27, 2014.

(51) Int. Cl.
*A61M 39/28* (2006.01)
*A61M 5/168* (2006.01)
(Continued)

(52) U.S. Cl.
CPC ........ *A61M 39/281* (2013.01); *A61M 5/1684* (2013.01); *A61M 5/36* (2013.01);
(Continued)

(58) Field of Classification Search
CPC .. A61M 2202/0007; A61M 2202/0415; A61M 2205/3306; A61M 2205/3386;
(Continued)

(56) References Cited

U.S. PATENT DOCUMENTS

| | | | |
|---|---|---|---|
| 7,327,273 B2 | 2/2008 | Hung et al. | |
| 2005/0234407 A1* | 10/2005 | Spohn | A61G 7/0503 604/253 |
| 2014/0283620 A1 | 9/2014 | Kilko et al. | |

FOREIGN PATENT DOCUMENTS

| | | |
|---|---|---|
| WO | 97/37704 A1 | 10/1997 |
| WO | 9737704 A1 | 10/1997 |

(Continued)

OTHER PUBLICATIONS

PCT/IB2015/001034, "International Search Report" dated Sep. 18, 2015, 8 pages.

(Continued)

*Primary Examiner* — Brandy S Lee
(74) *Attorney, Agent, or Firm* — Bereskin & Parr LLP/S.E.N.C.R.L., s.r.l.; Tony Orsi

(57) ABSTRACT

Methods and devices for monitoring and/or controlling delivery of a fluid to a patient monitor a level of the fluid and generate an alarm and/or block flow of the fluid through a flexible delivery tube to the patient in response to detecting that the fluid level has dropped below a predetermined level. A device for monitoring and/or controlling delivery of the fluid to a patient is removeably mountable to a fluid delivery assembly having the delivery tube. When the device is configured to control delivery of the fluid, the device automatically reconfigures from a first configuration in which fluid is allowed to flow through the delivery tube to a second configuration in which the delivery tube is in a deformed state via the device to block flow of fluid through the (Continued)

delivery tube upon the device detecting that the fluid level is below the predetermined level.

18 Claims, 9 Drawing Sheets

(51) Int. Cl.
*A61M 5/36* (2006.01)
*A61M 5/14* (2006.01)
*A61M 5/40* (2006.01)

(52) U.S. Cl.
CPC ......... *A61M 39/285* (2013.01); *A61M 5/1411* (2013.01); *A61M 5/1685* (2013.01); *A61M 5/40* (2013.01); *A61M 2202/0007* (2013.01); *A61M 2202/0415* (2013.01); *A61M 2205/3306* (2013.01); *A61M 2205/3386* (2013.01)

(58) Field of Classification Search
CPC .............. A61M 39/281; A61M 39/285; A61M 5/1411; A61M 5/1684; A61M 5/1685; A61M 5/36; A61M 5/40
See application file for complete search history.

(56) References Cited

FOREIGN PATENT DOCUMENTS

| WO | 2007092637 A2 | | 8/2007 |
|---|---|---|---|
| WO | WO2007092637 | * | 8/2007 |
| WO | 2009039203 A2 | | 3/2009 |
| WO | 2009146405 A1 | | 12/2009 |
| WO | 2009146405 A2 | | 12/2009 |
| WO | 2015132676 A9 | | 11/2015 |

OTHER PUBLICATIONS

PCT/IB2015/001034, "Written Opinion of the International Searching Authority" dated Sep. 18, 2015, 4 pages.

* cited by examiner

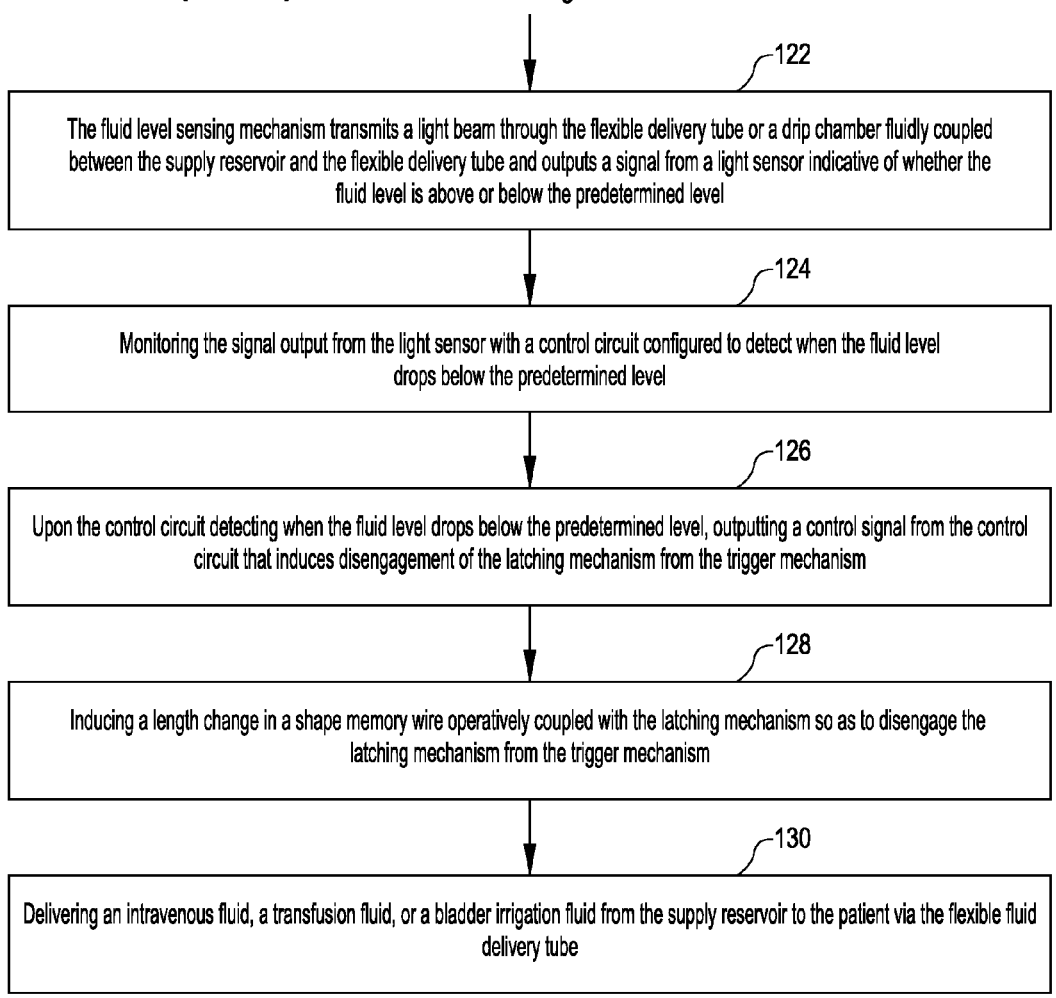

FLUID LEVEL MONITORING DEVICE

CROSS-REFERENCES TO RELATED APPLICATIONS

This application is a U.S. National Stage entry of PCT/IB2015/001034, filed Jan. 26, 2015, which claims priority to and the benefit of U.S. Provisional Application No. 61/932,144, entitled "FLUID LEVEL MONITORING DEVICE," filed Jan. 27, 2014, the full disclosures of which are incorporated herein by reference for all purposes.

BACKGROUND

A fluid (e.g., Intravenous (IV) fluid, bladder irrigation fluid, etc.) is often delivered to a patient via a fluid supply reservoir (e.g., an IV administration set, such as a gravity-fed IV drip bag) or a fluid infusion pump (e.g., an IV pump). A gravity-fed fluid delivery system typically includes a drip chamber (also referred to as a reservoir) and flexible tubing through which the fluid is delivered to a patient. When the IV fluid container or bag is empty, the drip chamber will run dry and the fluid flow will eventually stop. A large number of gravity-fed fluid drip bags used in the operating room (OR) or hospital ward environment run dry before being changed. Many gravity-fed fluid drip bags run dry undetected during high stress procedures where multiple lines and bags are in use, as is typically the case during complex surgery, emergency response or in ambulances.

When a fluid bag runs dry the patient can be exposed to increased risks. These risks when receiving IV fluids include: complications of clotting and obstruction of the IV catheter; possible awareness under general anesthesia if the IV line is being used to administer total intravenous anesthetic; and venous air embolism when the IV fluid bag is pressurized for rapid infusion as is often the case during emergency situations. While automatic infusion pumps are used in standard care wards and areas of "routine" care, they are expensive and time-consuming to program and as such are unsuitable for use in trauma, surgical or emergency use. Similarly, when a bag delivering fluid to a patient receiving continuous bladder irrigation runs dry, the risk of bleed and requirement for further surgical intervention is high. As such, improved methods and devices for controlling the delivery of IV fluid to a patient would be beneficial.

SUMMARY

Methods and devices are provided for monitoring and/or controlling delivery of a fluid to a patient, such as fluids delivered to a patient from an IV bag or a continuous bladder irrigation system. The methods and devices monitor a level of a fluid delivered to a patient and trigger an alarm and/or block flow of fluid through a flexible delivery tube in response to detection that the fluid level has dropped below a predetermined level, thereby notifying a health care practitioner that the fluid level has dropped below the predetermined level and/or preventing the potential risk associated with not blocking continued flow of fluid through the flexible delivery tube.

While example methods and devices are described herein with respect to monitoring and/or controlling of delivery of a fluid to a patient using an IV drip bag, the methods and devices described herein can be applied to control delivery of any suitable fluid (including but not limited to IV fluids) through any type of fluid delivery system (including but not limited to IV drip bags and IV pumps). For example, the methods and devices described herein can be used to monitor and/or control delivery of fluid through fluid delivery tubes used in continuous bladder irrigation, transurethral resections, transfusion sets, and arterial pressurized catheter lines in interventional radiology procedures among others.

Thus, in one aspect, a method is provided for monitoring and/or controlling delivery of a fluid to a patient through a flexible fluid delivery tube. The method includes providing a fluid-flow monitoring and/or control device removeably mountable to a fluid delivery system configured to deliver the fluid to the patient. The fluid delivery system includes the flexible fluid delivery tube. The fluid-flow control device includes a fluid level sensing mechanism. The fluid level sensing mechanism is used to detect when a fluid level of the fluid supplied to the patient drops below a predetermined level. In response to the detection of the fluid level dropping below the predetermined level: 1) an alarm is generated indicating that the fluid level has dropped below the predetermined level, and/or 2) a flow control mechanism is reconfigured from a first configuration in which flow of the fluid through the fluid delivery system is not blocked to a second configuration in which the flow of the fluid through the fluid delivery system is blocked. The method can optionally include any suitable combination of additional acts as described herein.

In another aspect, a device is provided for monitoring and/or controlling delivery of a fluid to a patient through a flexible fluid delivery tube. The device includes a fluid level sensing mechanism. The fluid level sensing mechanism is configured to detect when a fluid level of the fluid supplied to the patient drops below a predetermined level. The device is removeably mountable to a fluid delivery system configured to deliver the fluid to the patient. The fluid delivery system includes the flexible fluid delivery tube. The device generates an alarm and/or blocks flow of fluid through the flexible fluid delivery tube in response to detecting when the fluid level drops below the predetermined level. In many embodiments, the device is removeably mountable to the flexible fluid delivery tube.

The device can include a flow control mechanism to block the flow of fluid through the flexible delivery tube. The flow control mechanism can be operatively coupled with the fluid sensing mechanism and configured to, in response to the detection of the fluid level dropping below the predetermined level, reconfigure from a first configuration in which flow of the fluid through the flexible delivery tube is not blocked to a second configuration in which the flow of the fluid through the flexible deliver tube is blocked.

In many embodiments, the fluid sensing mechanism includes a light transmitter and a light sensor. The light transmitter can be configured to transmit a beam a light through the flexible delivery tube or a drip chamber that is in fluid communication with the flexible delivery tube. The light sensor can be configured to output a signal indicative of an amount of the light beam incident on the light sensor, the amount of light incident being indicative of whether the fluid level is above or below the predetermined level.

In many embodiments, the device includes a control circuit. The control circuit can be configured to, in response to detecting when the fluid level drops below the predetermined level, output a control signal that induces reconfiguration of the flow control mechanism from the first configuration to the second configuration.

In many embodiments, the flow control mechanism, when reconfigured from the first configuration to the second configuration, deforms the flexible deliver tube to block flow of the fluid through the flexible delivery tube. For example, the flow control mechanism can include an interface surface reconfigurable from a first position and/or orientation to a second position and/or orientation in which the interface surface interfaces with the flexible delivery tube so as to deform the flexible delivery tube. As a more specific example, the interface surface can be an external surface of a non-cylindrical length of a rotatable shaft that is rotated during reconfiguration of the flow control mechanism from the first configuration to the second configuration.

In many embodiments, the device includes a trigger operatively coupled with the flow control mechanism and reconfigurable from a non-actuated configuration in which the flow control mechanism is in the second configuration to an actuated configuration in which the flow control mechanism is in the first configuration to enable delivery of the fluid to the patient through the flexible delivery tube. The device can include a latching mechanism configured to be engaged with the trigger to retain the trigger in the actuated configuration prior to the detection of the fluid level dropping below the predetermined level. The trigger can be operatively coupled with a spring mechanism configured to bias the trigger towards the non-actuated configuration. The device can be configured such that disengagement of the latching mechanism from the trigger reconfigures the flow control mechanism from the first configuration to the second configuration.

In many embodiments, the fluid level sensing mechanism transmits a light beam through the flexible delivery tube or a drip chamber that is in fluid communication with the flexible delivery tube and outputs a signal from a light sensor indicative of whether the fluid level is above or below the predetermined level. The device can include a control circuit that monitors the signal output from the light sensor to detect when the fluid level drops below the predetermined level and outputs a control signal that induces disengagement of the latching mechanism from the trigger upon detecting when the fluid level drops below the predetermined level. For example, the control signal output from the control circuit can be used to induce a length change in a shape memory wire operatively coupled with the latching mechanism so as to disengage the latching mechanism from the trigger.

The device can be used to control the delivery of any suitable fluid to a patient. For example, the device can be used to control delivery of an intravenous fluid, a medication fluid, intravenous nutritional fluid, a blood transfusion fluid, or a bladder irrigation fluid to the patient via the flexible fluid delivery tube.

The device can be attachable to an IV delivery set, such as an IV drip bag used to deliver fluids (e.g., intravenous medications) to a patient. The device can monitor the level of fluid in an IV reservoir or drip chamber attached to the IV drip bag and determine when the IV drip bag is running dry. In the illustrated embodiment, components in the device housing monitor the level of fluid in the IV reservoir and regulate the flow of the fluid through the tube connected to the IV reservoir. A trigger, such as one that can be pushed into the body of the device housing, activates the device. A secondary activation may also exist in the form of an electronic switch. A pivot catch can be used to engage with the trigger when the trigger is pushed into the body of the device housing, thereby holding the trigger in the activated position. While the trigger is in the activated position, fluid is allowed to flow through the tube to the patient without being impeded by the device.

In many embodiments, a sensor system is used to monitor fluid level during fluid delivery. The sensor system can include a transmitter and a light sensor in combination with a reflector to monitor a level of the fluid delivered from the fluid reservoir. In the illustrated embodiment, the intensity of light measured by the light sensor drops below a predetermined level when the level of fluid in the fluid reservoir drops below a stipulated amount. The light sensor sends signals based on the intensity of light measured by the light sensor that can trigger an event, such as an alarm, when the fluid level is low. In the illustrated embodiment, the light sensor sends signals to one or more components on a printed circuit board that analyze the signals and based on the signals received, trigger an alarm event. In the illustrated embodiment, the components on the printed circuit board send a signal to a connector or wire connected to the printed circuit board when an alarm state is triggered. In some embodiments, the signal can also sound an audible alarm, such as via a speaker connected to the printed circuit board, notifying a practitioner that the fluid drip bag is running low on fluid.

A connector or wire can be used to control the activation of a shut off or pinch off mechanism to stop the flow of fluid through the flexible delivery tube from the fluid reservoir bag. In some embodiments, the wire is composed of a material that is controllably shortened to trigger this shut off mechanism. For example, this wire can be composed of a shape-memory alloy, such as nickel titanium alloy or 'Nitinor'. This connector or wire will be referred to throughout as a nitinol wire, though it is understood that other designs and materials could be used for this connector. In the illustrated embodiment, the nitinol wire shortens in length when an electrical signal is passed through it. The nitinol wire can be connected to the pivot catch on one end and to the IV device housing on the other end. In many embodiments, the Nitinol wire extends between the pivot catch and the control circuit, which can be constituted as a printed circuit board (PCB) assembly. The PCB assembly can currently be manufactured complete with the Nitinol wire and pivot latch attached as one sub-assembly. In many embodiments, the Nitinol wire is connected, on both ends, to something that can conduct electricity. Accordingly, in embodiments in which the Nitinol wire is connected to the device housing, a wire can be used to connect electrical connect the end of the Nitinol wire connected to the device housing to the PCB assembly. The shortening of the nitinol wire can be used to cause the pivot catch to disengage from the trigger. The trigger can be connected to a resilient structure, such as a trigger spring. In many embodiments, the tension in the trigger spring is increased when the trigger is pushed into the activated position. When the trigger is disengaged from the pivot catch, the tension in the trigger spring pulls the trigger back to the deactivated position.

The trigger system described above can be designed to cause the shut off mechanism to restrict or shut off fluid flow through the tube of the IV bag. In the illustrated embodiment, a moveable pinching member is connected to the trigger to pinch the tube closed. This pinching member can be half-moon shaped, in some embodiments, and is referred to herein as a half-moon bar. The half-moon bar is operatively coupled with the trigger, such that when the trigger is in the activated position, the half-moon bar is in the open position, and when the trigger is in the deactivated position the half-moon bar is in the closed position. In the open position the half-moon bar allows fluid to flow through the tube connected to the IV reservoir. When in the closed position, the half-moon bar pinches the tube connected to the IV reservoir thereby restricting the flow of fluid through the tube. Thus, the IV device can monitor the level of fluid in an IV drip bag, notify a practitioner when an IV drip bag is running low and/or regulates the flow of fluid through the tube connected to the IV drip bag.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

In the following description of the present embodiments, reference is made to the accompanying drawings that form a part hereof, and in which is shown by way of illustration specific embodiments in which the embodiments may be practiced. These embodiments are described in sufficient detail to enable those skilled in the art to practice the invention, and it is to be understood that other embodiments may be utilized and that process, electrical or mechanical changes may be made without departing from the scope of the present disclosure. The following detailed description is, therefore, not to be taken in a limiting sense.

Figure 1:
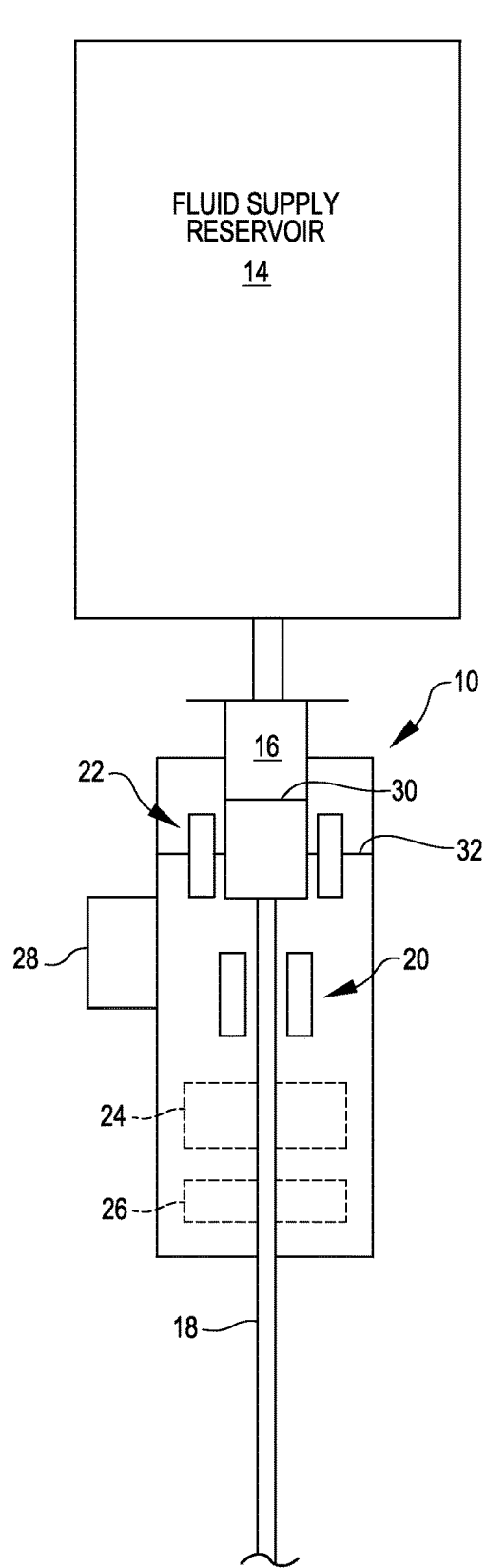
FIG. 1 is a schematic diagram of embodiments of a device for monitoring and/or controlling delivery of a fluid shown attached to a fluid delivery system that includes a flexible delivery tube, in accordance with many embodiments.

Turning now to the drawings in which like reference numbers refer to like elements in the various figures, FIG. 1 shows a schematic representation of a device 10 that is removeably attachable to any suitable fluid delivery system that delivers a fluid to a patient via a flexible fluid delivery tube. For example, FIG. 1 shows a fluid delivery system 12 that includes a fluid supply reservoir 14, a drip chamber 16 that is in fluid communication with the fluid supply reservoir 14, and a flexible fluid delivery tube 18 fluidly coupled with the drip chamber 16 for delivering fluid supplied from the fluid supply reservoir 14 to a patient. In the illustrated embodiment, the device 10 includes a flow control mechanism 20, a fluid level sensing mechanism 22, a control unit 24, a power source 26, and an actuation trigger 28.

In many embodiments, the flow control mechanism 20 is configured to be removeably coupled to the flexible fluid delivery tube 18 so as to support the device 10 when the device is coupled with the tube 18. The flow control mechanism 20 is controllably reconfigurable to at least a first configuration in which the flexible fluid delivery tube 18 is not deformed sufficiently by the flow control mechanism 20 to block flow of fluid through the flexible fluid delivery tube 18 and a second configuration in which the flexible fluid delivery tube 18 is deformed sufficiently by the flow control mechanism 20 to block flow of fluid through the flexible fluid delivery tube 18.

In many embodiments, the fluid level sensing mechanism 22 is configured to detect whether a fluid level within the fluid delivery system 12 is above or below a predetermined level. For example, in the illustrated embodiment, the fluid level sensing mechanism 22 is configured to detect whether a fluid level 30 is above or below a predetermined fluid level. In the illustrated embodiment, the device 10 has an indicator line 32 that indicates the location of the predetermined fluid level 32 with respect to the device 10. In many embodiments, the fluid level sensing mechanism 22 outputs a signal indicative of whether the fluid level 30 within the drip chamber 16 is above or below the indicator line 32. In alternate embodiments, the fluid level sensing mechanism can be configured to detect whether the fluid level within the delivery tube 18 is above or below a predetermined level, thereby permitting use where the fluid delivery system does not include a drip chamber 16.

The control unit 24 monitors the output of the fluid level sensing mechanism 22 to detect if the fluid level 30 has dropped below the predetermined level, thereby detecting when the fluid supply reservoir 14 has run dry. Upon detecting that the fluid level 30 has dropped below the predetermined level, the control unit 24 induces reconfiguration of the flow control mechanism 20 from the first configuration to the second configuration, thereby blocking further flow of the fluid through the delivery tube 18.

The actuation trigger 28 is operatively coupled with the flow control mechanism 20. The actuation trigger 28 is used to reset the flow control mechanism 20 from the second configuration (in which fluid flow is blocked) back to the first configuration (in which fluid flow is not blocked) so as to enable delivery of fluid to the patient via the delivery tube 18. For example, prior to attaching the device 10 to a flexible fluid delivery tube 18, the actuation trigger 28 is depressed to reconfigure the flow control mechanism 20 to the first configuration. In many embodiments, a spring assembly is operatively coupled with the actuation trigger 28 to bias the actuation trigger and the flow control mechanism towards the second configuration (in which flow is blocked). In many embodiments, a latching mechanism latches the actuation trigger 28 and the flow control mechanism 20 in the first configuration until the control unit 24 induces release of the latching mechanism in response to detecting when the fluid level has dropped below the predetermined level, thereby reconfiguring the flow control mechanism 20 into the second configuration to block further flow of the fluid through the delivery tube 18.

Figure 2:
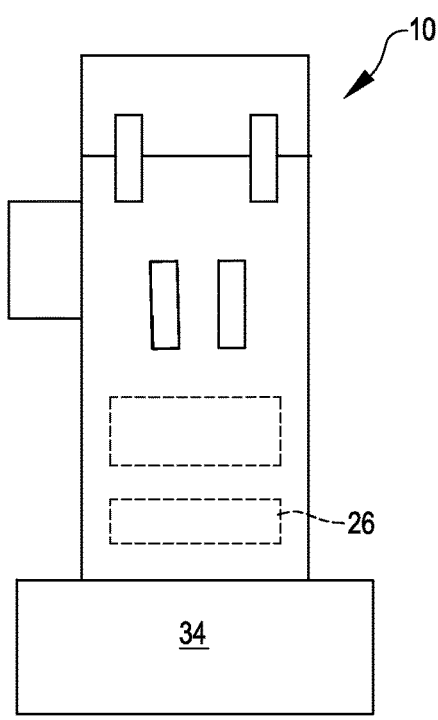
FIG. 2 is a schematic diagram of the device of FIG. 1 shown coupled to a recharging station for recharging the device, in accordance with many embodiments.

The power source 26 supplies power to operate the device 10. Any suitable power source 26 can be used, such as one or more batteries, one or more replaceable batteries, and/or one or more rechargeable batteries, or long life lithium ion batteries. For example, FIG. 2 shows the device 10 coupled with a recharging station 34 configured to recharge the power source 26 when the power source 26 includes one or more rechargeable batteries.

Figure 3:
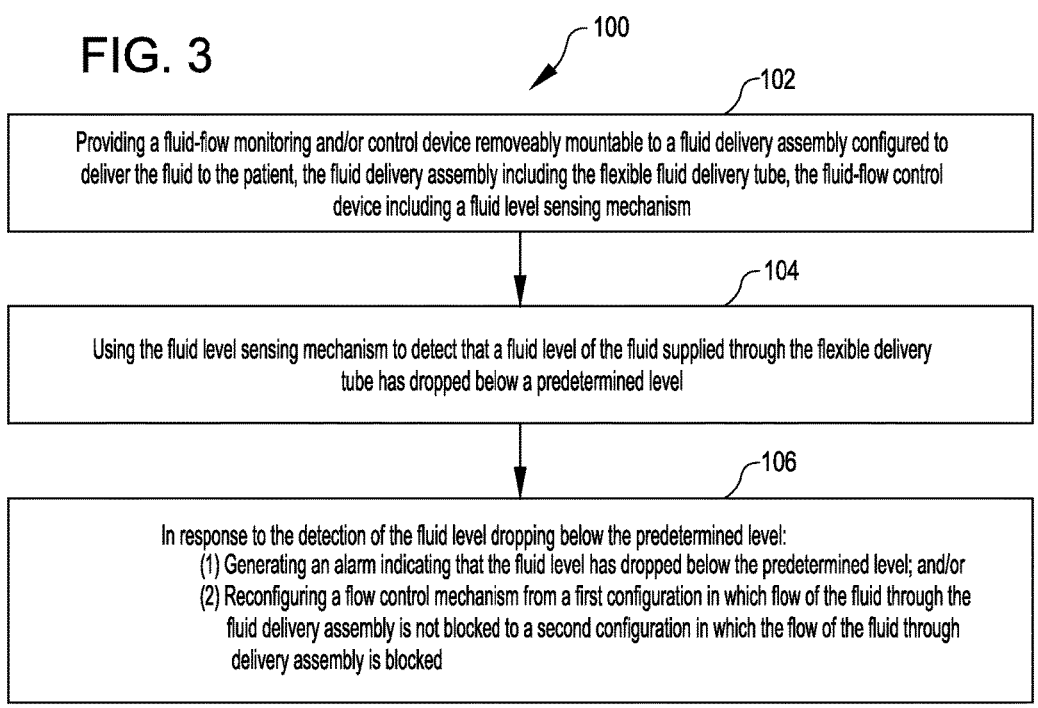
FIG. 3 is a block diagram of acts of a method for monitoring and/or controlling delivery of a fluid to a patient through a flexible fluid delivery tube, in accordance with many embodiments.

FIG. 3 is a simplified block diagram of acts of a method 100 for monitoring and/or controlling delivery of a fluid to a patient through a flexible fluid delivery tube, in accordance with many embodiments. Any suitable device, including any suitable device described herein such as the device 10, can be used to practice the method 100.

The method 100 includes providing a fluid-flow control device removeably mountable to a fluid delivery system configured to deliver the fluid to the patient (act 102). The fluid delivery system includes the flexible fluid delivery tube. The fluid-flow control device including a fluid level sensing mechanism. The fluid level sensing mechanism is used to detect that a fluid level of the fluid supplied through the flexible delivery tube has dropped below a predetermined level (act 104). In response to the detection of the fluid level dropping below the predetermined level: (1) an alarm is generated indicating that the fluid level has dropped below the predetermined level; and/or (2) a flow control mechanism is reconfigured from a first configuration in which flow of the fluid through the fluid delivery system is not blocked to a second configuration in which the flow of the fluid through the fluid delivery system is blocked (act 106).

Figure 4:
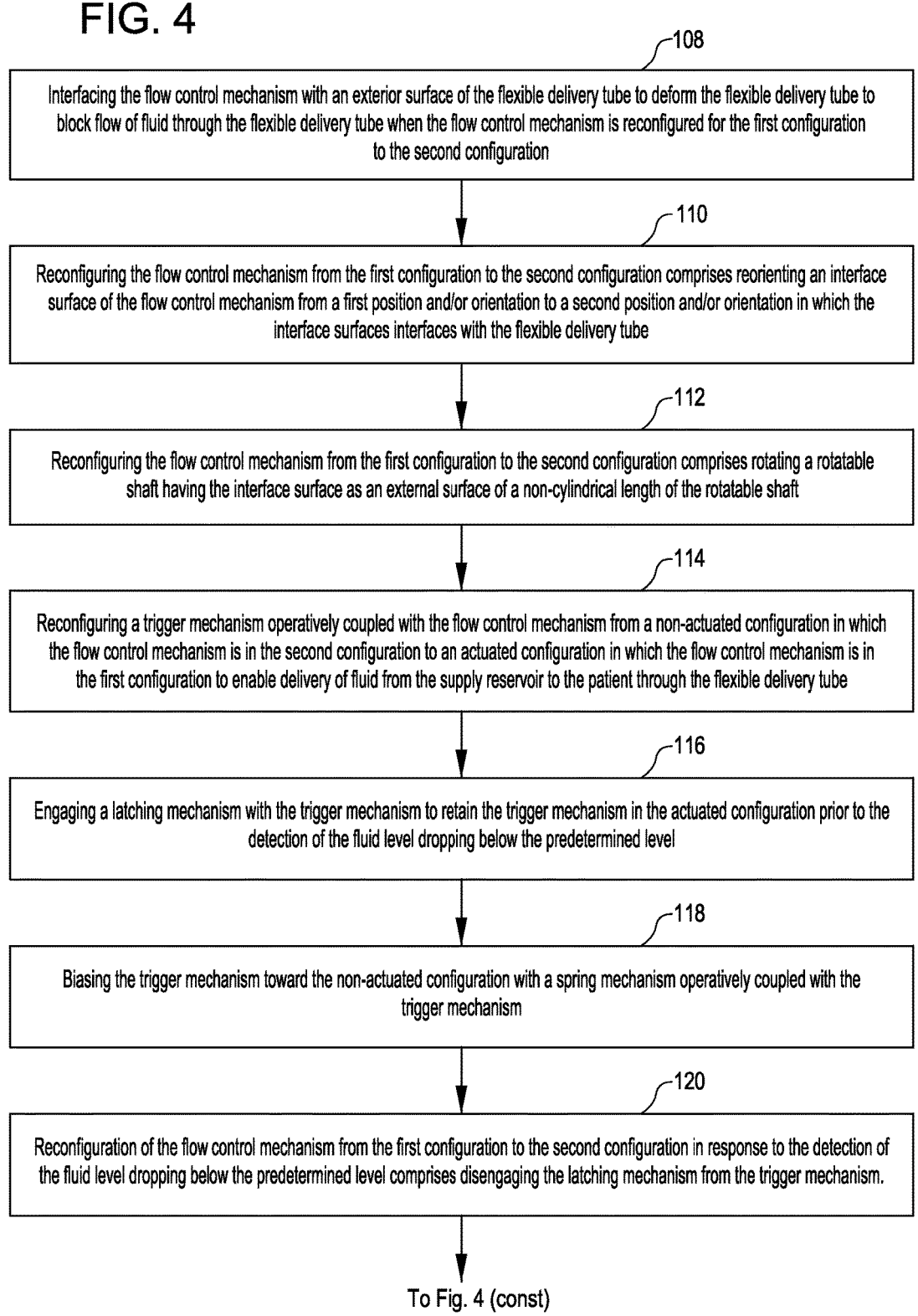
FIG. 4 is a block diagram of additional optional acts that can be accomplished in the method of FIG. 3, in accordance with many embodiments.

FIG. 4 is a simplified block diagram of additional optional acts that can be accomplished in the method 100, in accordance with many embodiments. For example, the method 100 can further include interfacing the flow control mechanism with an exterior surface of the flexible delivery tube to deform the flexible delivery tube to block flow of fluid through the flexible delivery tube when the flow control mechanism is reconfigured from the first configuration to the second configuration (act 108). For example, reconfiguring the flow control mechanism from the first configuration to the second configuration can include reorienting an interface surface of the flow control mechanism from a first position and/or orientation to a second position and/or orientation in which the interface surface interfaces with the flexible delivery tube (act 110). As a more specific example, reconfiguring the flow control mechanism from the first configuration to the second configuration can include rotating a rotatable shaft having the interface surface as an external surface of a non-cylindrical length of the rotatable shaft (act 112).

The method 100 can include reconfiguring a trigger operatively coupled with the flow control mechanism from a non-actuated configuration in which the flow control mechanism is in the second configuration to an actuated configuration in which the flow control mechanism is in the first configuration to enable delivery of the fluid to the patient through the flexible delivery tube (act 114). A latching mechanism can be engaged with the trigger to retain the trigger in the actuated configuration prior to the detection of the fluid level dropping below the predetermined level (act 116). The trigger can be biased towards the non-actuated configuration with a spring mechanism operatively coupled with the trigger (act 118). Reconfiguration of the flow control mechanism from the first configuration to the second configuration in response to the detection of the fluid level dropping below the predetermined level can include disengaging the latching mechanism from the trigger (act 120).

The fluid level sensing mechanism can transmit a light beam through the flexible delivery tube or a drip chamber fluidly coupled with the flexible delivery tube and outputs a signal from a light sensor indicative of whether the fluid level is above or below the predetermined level (act 122). The signal output from the light sensor can be monitored with a control circuit configured to detect when the fluid level drops below the predetermined level (act 124). Upon the control circuit detecting when the fluid level drops below the predetermined level, a control signal can be output from the control circuit that induces disengagement of the latching mechanism from the trigger mechanism (act 126). For example, the control signal can be used to induce a length change in a shape memory wire operatively coupled with the latching mechanism so as to disengage the latching mechanism from the trigger mechanism (act 128).

The method 100 can be used to control the delivery of any suitable fluid to a patient. For example, the method 100 can include delivering an intravenous fluid, a medication fluid, intravenous nutritional fluid, a blood transfusion fluid, or a bladder irrigation fluid from the supply reservoir to the patient via the flexible fluid delivery tube (act 130).

Figure 5:
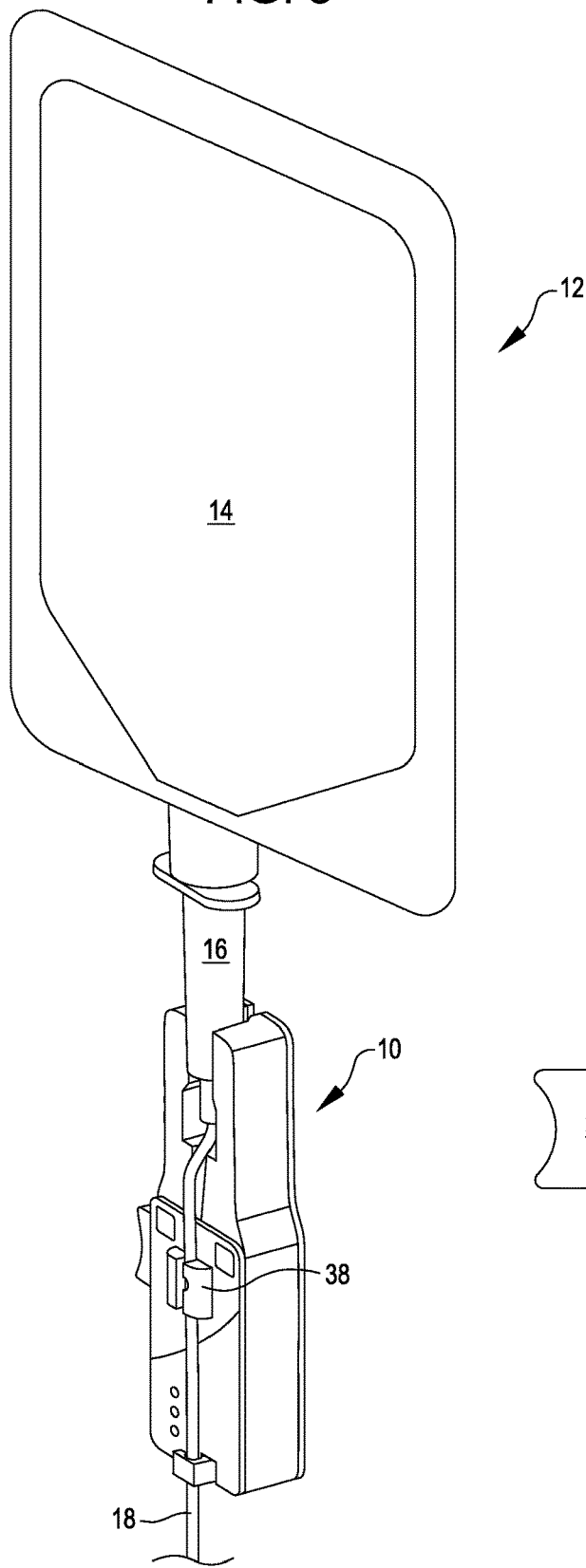
FIG. 5 illustrates a device for monitoring and controlling delivery of fluid to a patient through a flexible fluid delivery tube shown attached to a fluid delivery system that includes the flexible fluid delivery tube, according to an embodiment.

FIG. 5 illustrates an example embodiment of the device 10 for monitoring and controlling delivery of fluid to a patient through a flexible fluid delivery tube shown attached to a fluid delivery system 12 that includes the flexible fluid delivery tube 18. The device 10 is removeably attachable to fluid delivery system 12. The fluid delivery system 12 can be any suitable fluid delivery system, such as an IV drip bag delivery set used to deliver fluids (e.g., intravenous medications, saline solution, Ringer's lactate solution, fluids providing nutrition, buffer solutions, among other fluids) to a patient. The illustrated fluid delivery system 12 includes a fluid supply reservoir 14 and a flexible fluid delivery tube 18. The fluid supply reservoir 14 holds the fluid to be delivered to the patient. In the illustrated example, the fluid supply reservoir 14 is a gravity-fed IV drip bag, where gravity is used to assist in the delivery of the fluid to the patient. In another example, a pump is used to assist in the delivery of the fluid in the fluid supply reservoir 14 to the patient. The drip chamber 16 is fluidly coupled with the fluid supply reservoir 14. The drip chamber 16 is configured to allow gases trapped within the chamber to rise above the fluid to facilitate passing of the fluid down the delivery tube 18, as well as regulating the flow of the fluid through the delivery tube 18. The delivery tube 18 is fluidly connected to the drip chamber 16 and carries fluid from the drip chamber 16 to the patient. In some embodiments, the delivery tube 18 is directly connected to the fluid supply reservoir 14 and not to the drip chamber 16.

Figure 6:
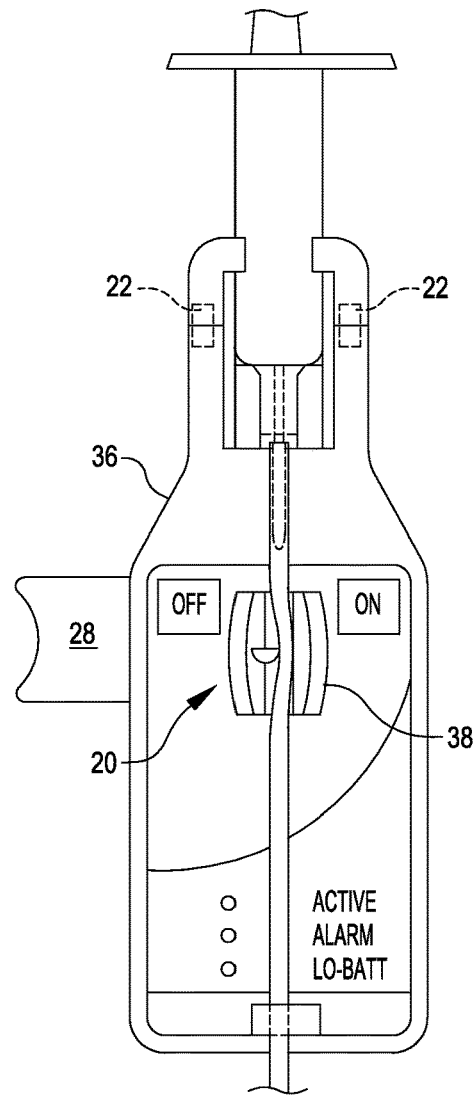
FIG. 6 is a front view illustration of the device of FIG. 5 in a configuration in which the flexible fluid delivery tube is held in a deformed state by a flow control mechanism of the device so as to block flow of the fluid through the flexible fluid delivery tube.
Figure 7:
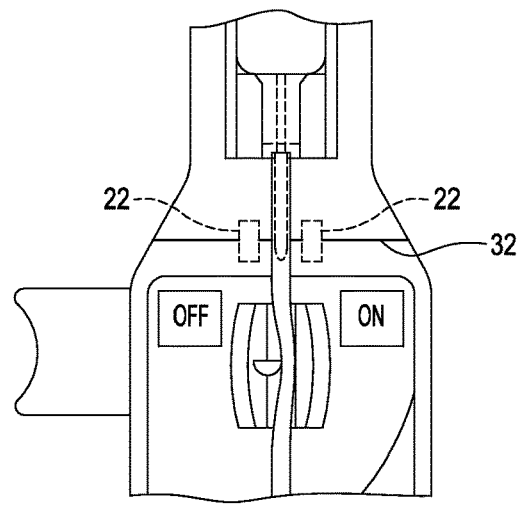
FIG. 7 is a front view illustration of an alternate embodiment of the device of FIG. 5 that includes a fluid level sensor configured to detect when a fluid level within the flexible fluid delivery tube drops below a predetermined level, according to an embodiment.

In the illustrated embodiment, the device 10 determines when a fluid supply reservoir 14 associated with the delivery tube 18 runs low, by monitoring the level of fluid in the drip chamber 16. The fluid level sensing mechanism 22 helps detect the level of fluid in the drip chamber 16, as described in greater detail in conjunction with FIG. 6. In another embodiment, the device 10 monitors the level of fluid in the delivery tube 18, particularly when the delivery tube 18 is directly connected to the fluid supply reservoir 14, and no drip chamber 16 is present. FIG. 7 illustrates an embodiment in which the fluid sensing mechanism 22 is configured to monitor the level of fluid in the delivery tube 18 to sense when the fluid level drops below the predetermined fluid level indicator line 32.

In the illustrated embodiment, the device 10 includes a device housing 36. The device housing 36 includes components that monitor the level of the fluid in the drip chamber 16 and control the flow of fluid through the delivery tube 18. The device housing 36 is configured to attach to the delivery tube 18 and drip chamber 16. In the illustrated embodiment, the device housing 36 includes a tube seat 38 for securely holding the delivery tube 18 and attaching the device housing 36 to the delivery tube 18. The delivery tube 18 is passed through the tube seat 38. The tube seat 38 may be configured to partially cover the surface of the delivery tube 18 without impeding the flow of fluid through the delivery tube 18. The tube seat 38 provides a friction fit sufficient to allow the device 10 to hang on the delivery tube 18 below the fluid supply reservoir 14.

The device housing 36 includes a trigger 28 for activating the device 10. In the illustrated embodiment, a practitioner activates the device 10 by pushing the trigger 28 horizontally into the body of the device housing 36, placing the trigger 28 in an activated position. In one example, when the trigger 28 is in the activated position, the fluid control mechanism 20 is held in an open position allowing fluid to flow through the deliver tube 18 as described in greater detail in conjunction with FIG. 10 and FIG. 11. Similarly, when the trigger 28 is in the de-activated position (the trigger is substantially outside the body of the device housing 36) the flow control mechanism 20 is configured to be in a closed position, pinching the delivery tube 18 thereby preventing the flow of fluid through the delivery tube 18 as described in greater detail in conjunction with FIG. 10 and FIG. 11. In the illustrated embodiment, the trigger 28 is at least partially colored (e.g., bright red or yellow), such that when the trigger 28 is in the activated position the color on the trigger 28 is not or less visible, making it obvious to an observer whether the trigger 28 is activated or not.

Once activated, components of the device 10 may reset the trigger 28 to the deactivated position on detecting that the level of fluid in the drip chamber 16 or the delivery tube 18 has dropped below a predetermined level, as described in greater detail in conjunction with FIG. 10 and FIG. 11 below. In addition to resetting the trigger 28, the device 10 can sound an audible alarm alerting the practitioner that the fluid level in the drip chamber 16 or within the delivery tube 18 has dropped below a predetermined level. In the illustrated embodiment, in addition to sounding an alarm, the device 10 may send a signal via a network, such as a WiFi, BLUETOOTH® or GSM signal or other transmission protocol or system, to a patient monitoring system, mobile phone, pager, etc., notifying these systems that the fluid supply reservoir 14 has run dry. In some examples, the device 10 includes one or more visual indicators, such as light-emitting diodes (LED) or alarms. The LEDs may indicate the status of the device 10, such as whether the device 10 has been activated, whether the device 10 is sufficiently powered or whether the device 10 has been turned on. The alarms may generate an audible sound based on the level of fluid identified in the drip chamber 16. Thus, the device 10 may be used in concurrence with a fluid supply reservoir 14 to monitor the level of fluid in the fluid supply reservoir 14, determine when a fluid supply reservoir 14 runs dry or is on the verge of running dry, and notify a practitioner that the fluid supply reservoir 14 has run low.

Figure 8:
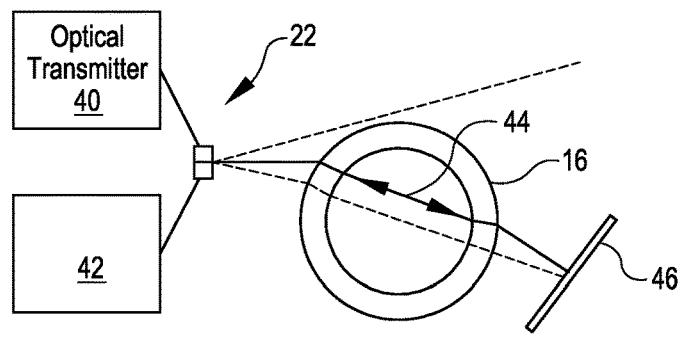
FIG. 8 and FIG. 9 are cross section view illustrations of a fluid level sensing mechanism for detecting when the fluid level drops below the predetermined level and includes a light transmitter and a light sensor, according to an embodiment.
Figure 9:
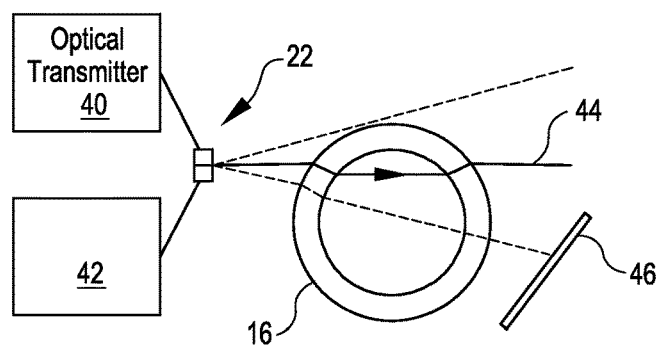

FIG. 8 and FIG. 9 illustrate a fluid level sensing mechanism 22 configured to detect whether the level of the fluid within the drip chamber 16 is above or below a predetermined level, according to one embodiment. In FIG. 8, the fluid level in the drip chamber 16 is above a predetermined level, thereby indicating that the fluid supply reservoir 14 has not run dry. In the illustrated embodiment, an optical transmitter 40 and a light sensor 42 in combination with a reflector 46 are used to determine if the level of fluid in the drip chamber 16 is above the predetermined level. The optical transmitter 40 periodically transmits light 44 through the drip chamber 16. In the illustrated embodiment, the light 44 transmitted by the optical transmitter 40 is infrared light (IR) light. The light sensor 42 periodically measures the intensity of the light 44 that falls on the light sensor 42. In one example, a voltage level is associated with the intensity of the light 44 measured by the light sensor 42.

When the drip chamber 16 has fluid above a predetermined level, the light 44 transmitted by the optical transmitter 40 lands on a reflector 46 present on the other side of the drip chamber 16. Any suitable component can be used as the reflector 46, such as, for example, a mirror, a prism reflector, and the like. In the illustrated embodiment, the reflector 46 is positioned and configured such that the light 44 transmitted by the optical transmitter is reflected back to the light sensor 42 when the fluid level in the drip chamber 16 is above the predetermined limit and is not reflected back to the light sensor 42 when the fluid level in the drip chamber 16 is below the predetermined limit. Since the refractive index of the fluid is much higher than that of air and very similar to the refractive index of the drip chamber 16 material, the light beam 44 is refracted by the first air-drip chamber interface, but is not refracted by a similar amount by the drip chamber-fluid interface. Thus, the light beam 44 inside the drip chamber 16 is significantly non-parallel to the light beam 44 initially transmitted by the optical transmitter 40, and the light beam 44 hits the reflector 46. The light beam 44 is incidentally reflected back by the reflector 46 to the light sensor 42. In the illustrated embodiment, the light sensor 42 measures the intensity of the light beam 46 incident on the light sensor 42.

In FIG. 9, the fluid in the drip chamber 16 is below the predetermined level. The light beam 44 transmitted by the optical transmitter 40 is refracted twice by the air-drip chamber interface both outside and inside the drip chamber 16. Since the inside and outside walls of the drip chamber 16 are locally parallel, the path of travel of the light beam 44 inside the drip chamber 16 is substantially parallel to the initial path of travel of the light beam 44 when it was transmitted by the optical transmitter 40. Similarly, the path of the refracted light beam 44 as it exits the drip chamber 16 is substantially parallel to the path of the light beam 44 initially transmitted by the optical transmitter 40, thereby causing the light beam 44 emitted by the optical transmitter 40 to miss the reflector 46. As the light beam 44 misses the reflector 46, the light sensor 42 measures a smaller intensity of light 44 than when there is fluid in the drip chamber 16 above a specified level, thereby identifying that the level of fluid in the drip chamber 16 is below a predetermined level.

FIG. 8 and FIG. 9 illustrate just one example of a fluid level sensing mechanism 22 that can be used with the device 10. Other sensor designs can also be used to detect low fluid level. Another example that could be used is provided in U.S. Pat. No. 7,327,273, filed on Feb. 11, 2005, and hereby incorporated by reference herein in its entirety.

Figure 10:
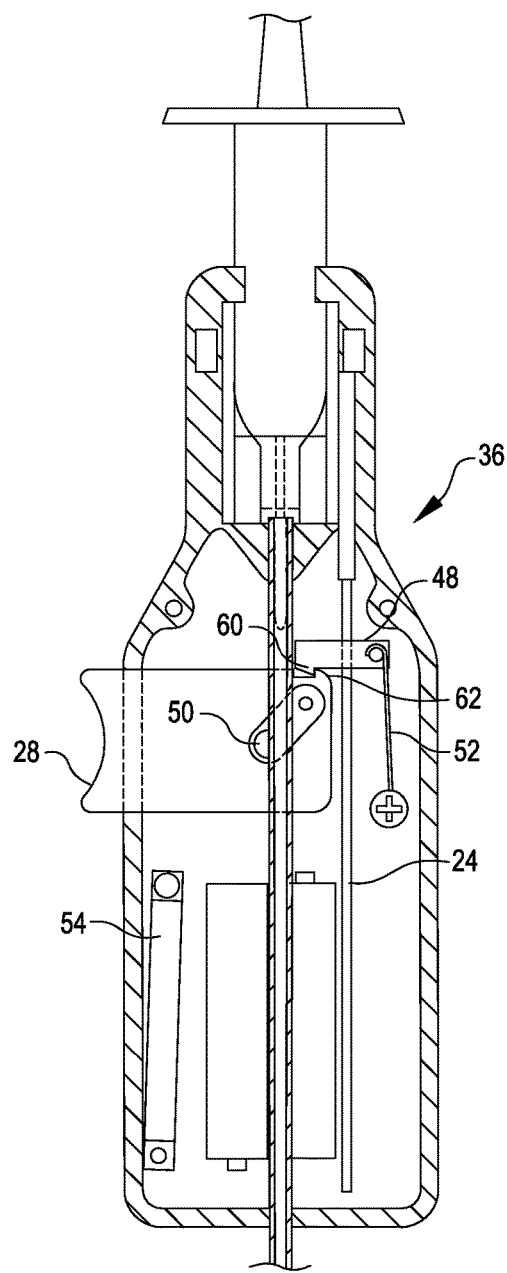
FIG. 10 shows an internal view of the device of FIG. 5 in an activated configuration.

FIG. 10 is an internal view of the device housing 36 in an activated position, according to one embodiment. The device 10 is activated when the trigger 28 is in the activated position. The device housing 36 in this embodiment includes a pivot catch 48, a half-moon bar 50, a printed circuit board (control unit 24), a nitinol wire 52, and a trigger spring 54. These are just some examples of components that can be included in the device 10, but more, fewer, or different components can be used, as well. The pivot catch 48 is configured to engage with, and hold on to the trigger 28, once the trigger 28 has been pushed into the activated position, thereby preventing the trigger 28 from releasing back to the deactivated position, as described in greater detail in conjunction with FIG. 11. Thus, when the trigger 28 is pushed into the activated position, the trigger 28 comes in contact with the pivot catch 48 and is held in the activated position by the pivot catch 48. Other trigger designs can also be used, including ones that the user engages by sliding a switch, rotating or spinning a rotatable member, or other mechanism of manipulation to activate the trigger 28. Similarly, the pivot catch 48 can be replaced with other mechanical mechanisms (e.g., rotatable, translatable, or bendable arms) for engaging with the trigger 28.

In the illustrated embodiment, the half-moon bar 50 is connected to the trigger 28, and substantially extends along a portion of the tube seat 38. The half-moon bar 50 is configured to impede the flow of fluid through the delivery tube 18 by pinching the delivery tube 18 when in the closed position, as described in conjunction with FIG. 11. When in the open position, the half-moon bar 50 no longer pinches the delivery tube 18, thereby allowing fluid to flow through the delivery tube 18. In the illustrated embodiment, the position of the half-moon bar 50 is controlled by the position of the trigger 28. When the trigger 28 is in the activated position, the half-moon bar 50 is moved into the open position, allowing fluid to flow through the delivery tube 18. Similarly, when the trigger 28 is in the deactivated position the half-moon bar 50 is in the closed position, impeding the flow of fluid through the delivery tube 18.

In the illustrated embodiment, the nitinol wire 52 is connected, on one end, to the end of the pivot catch 48, and on the other end to a stationary object such as a screw, a bolt, the printed circuit board or the device housing 36. The nitinol wire 52 is a shape memory alloy (SMA) and has the ability to undergo deformation when heated above a transformation temperature and recover to its un-deformed shape when the temperature of the SMA falls below the transformation temperature. In one example, when the nitinol wire 52 is heated above its transformation temperature the nitinol wire 52 deforms by shortening in length. In the illustrated embodiment, the nitinol wire 52 is configured to shorten in length when an electric signal is passed through the nitinol wire 52. The passage of the electric signal through the nitinol wire 52, results in the nitinol wire 52 being heated above its transformation temperature, causing the nitinol wire 52 to shorten in length.

The nitinol wire 52 is connected in this embodiment to a printed circuit board 24 or other similar type of component. In the illustrated embodiment, the fluid level sensing mechanism 22 sends a signal to the printed circuit board 24 based on the intensity level measured by the light sensor 42. In one example, the signal received by the printed circuit board 24 is below a specified value, thereby indicating that the level of fluid in the drip chamber 16 is below a predetermined level. The circuit on the printed circuit board 24 analyzes the signal from the light sensor 42, and based on the signal from the light sensor 42, triggers an alarm event. In the illustrated embodiment, the printed circuit board 24 includes one or more microcontrollers, logic switches, current sources, voltage sources, power sources, indicators, speakers, and/or regulators.

The components on the printed circuit board 24 determine whether the signal received from the light sensor 42 is below a specified level. In one embodiment, an alarm event is triggered when the signal received from the light sensor 42 is below a specified level. An alarm event being triggered indicates that the fluid level in the drip chamber 16 has dropped below a predetermined level and that the fluid supply reservoir 14 associated with the delivery tube 18 is running dry or is dry. In one embodiment, when an alarm event is triggered, speakers on the printed circuit board 24 sound an audible alarm indicating that the fluid supply reservoir 14 has run dry. In another embodiment, a set of indicators, such as a combination of LEDs or metrics (e.g., milliliters per hour) on one or more LCD displays indicate that an alarm event has been triggered and the fluid supply reservoir 14 has run dry.

In the illustrated embodiment, the printed circuit board 24 sends an electric signal through the nitinol wire 52 when an alarm event is triggered. The electrical signal may have a specified value and may run for a specified period of time. The electrical signal passing through the nitinol wire 52 causes the nitinol wire 52 to shorten in length. In the illustrated embodiment, the nitinol wire 52 is shortened by a threshold length or a threshold percentage of the length of the nitinol wire 52. For example, the nitinol wire 52 can shortened by 8% or more of the length of the nitinol wire 52. Other shape memory alloy wires can be used to replace the nitinol wire 52.

In the illustrated embodiment, the trigger spring 54 is connected to the trigger 28. The trigger spring 54 is configured such that when the trigger 28 is pushed into the activated position the tension in the trigger spring 54 increases. The tension in the trigger spring 54 causes the trigger spring 54 to return the trigger 28 to the deactivated position when the trigger 28 is released/disengaged from the pivot catch 48. Other resilient mechanisms can be used instead of the trigger spring 54 to perform a similar function, including the use of stretchable or bendable members.

Figure 11:
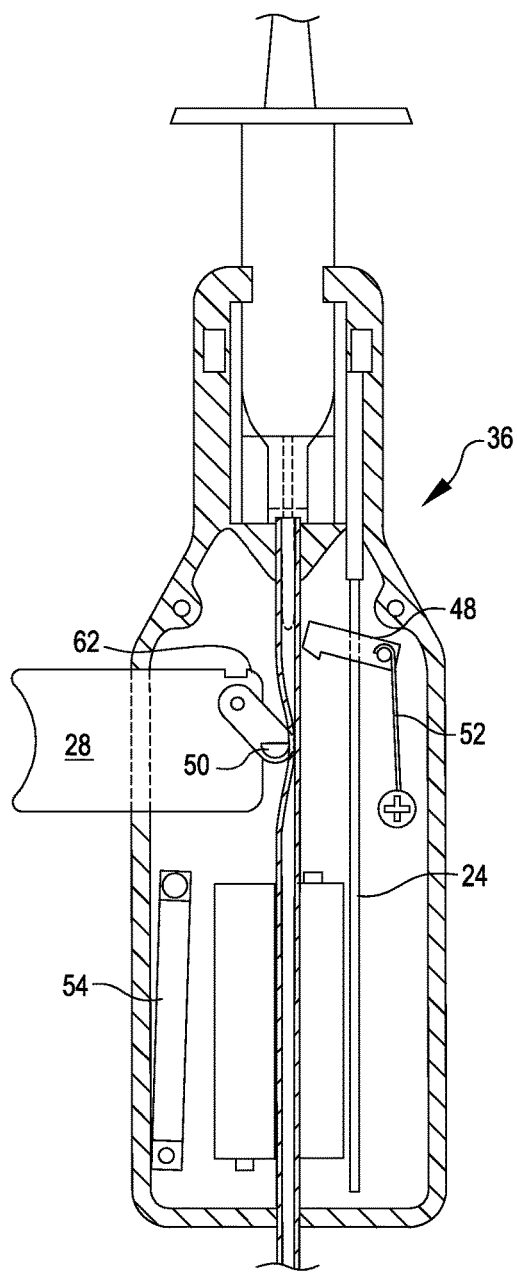
FIG. 11 shows an internal view of the device of FIG. 5 in a de-activated configuration.

FIG. 11 is an internal view of the device housing 36 in a de-activated position, according to the illustrated embodiment. The shortening of the nitinol wire 52 causes the pivot catch 48 attached to the nitinol wire 52 to rotate about its pivot in the direction of the nitinol wire 52. The rotation of the pivot catch 48 in the direction of the nitinol wire 52 results in the pivot catch 48 rising above a threshold value and disengaging from the trigger 28. The tension in the trigger spring 54 moves the disengaged trigger 28 from the activated position to the de-activated position. As the trigger 28 moves from the activated position to the deactivated position, the half-moon bar 50, attached to the trigger 28, is turned 90 degrees, from the open position to the closed position, thereby pinching the delivery tube 18 to prevent fluid from flowing through the delivery tube 18. Other pinching members can be used as well, such as pegs, pins, arms, or any structure that can be pushed against, rotated toward, or otherwise moved or translated into a position that pinches the delivery tube 18 to restrict or impede fluid flow.

Figure 12:
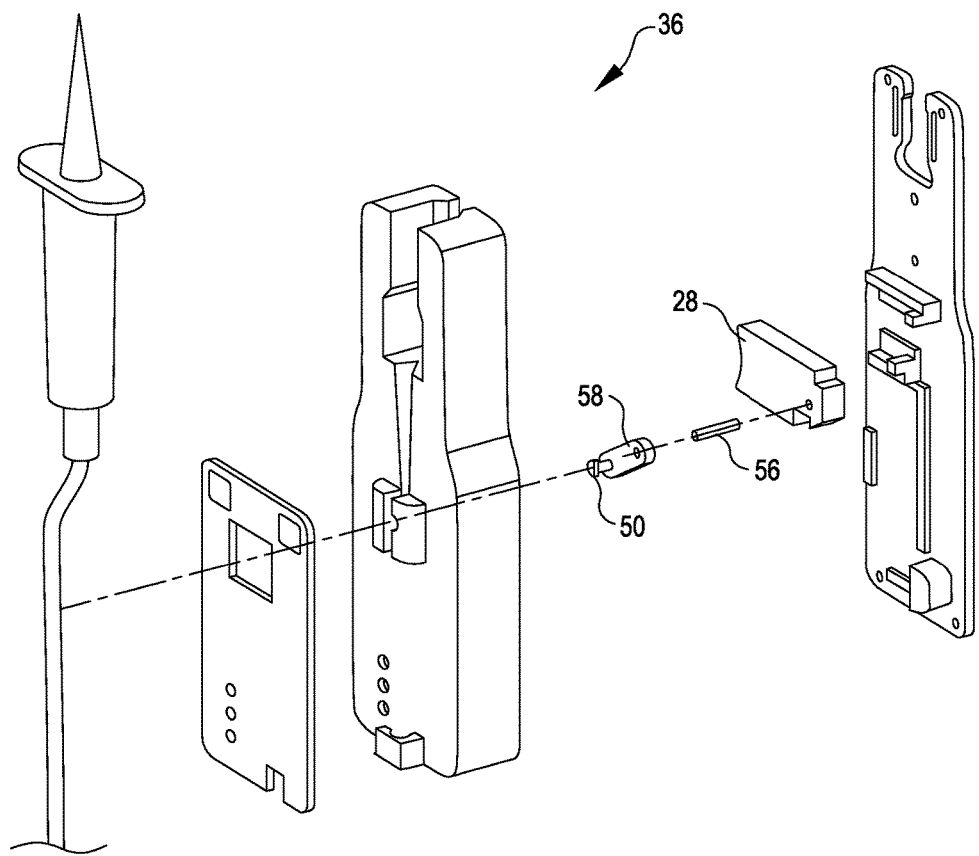
FIG. 12 is an exploded view of the components in the device of FIG. 5.

FIG. 12 is an exploded view of the components in the device housing 36, according to the illustrated embodiment. The trigger 28 is connected to the half-moon bar 50 via a half-moon bar shaft 56. A half-moon bar arm 58 connects the half-moon bar shaft 56 to the half-moon bar 50. Similar to that of a crank, the half-moon bar arm 58 is configured to rotate as the half-moon bar shaft 56 moves horizontally as the trigger 28 moves from the activated position to the deactivated position. The rotation of the half-moon bar arm 58 rotates the half-moon bar 50 by 90 degrees from the closed position to the open position or vise-versa. In the illustrated embodiment, the half-moon bar 50 is semi-cylindrical in shape, with the flat face of the half-moon bar 50 facing the delivery tube 18, and parallel to the delivery tube 18 in the open position. When the half-moon bar arm 58 rotates the half-moon bar 50 by 90 degrees, from the open position to the closed position, the flat face of the half-moon bar 50 rotates in the direction making the flat face of the half-moon bar 50 perpendicular to the delivery tube 18. As the flat face of the half-moon bar 50 becomes perpendicular to the delivery tube 18, the flat face of the half moon bar 50 pinches the delivery tube 18 preventing the flow of fluid through the delivery tube 18.

FIG. 10 illustrates the pivot catch 48 engaged to the trigger 28, according to the illustrated embodiment. A pivot catch lip 60 extends gradually from the body of the pivot catch 48. In the illustrated embodiment, the outer surface of the pivot catch lip 60 is gradually curved, while the inner surface of the pivot catch lip 60 is substantially perpendicular to the body of the pivot catch 48. Similarly a trigger lip 62 extends gradually from the body of the trigger 28. In the illustrated embodiment, the outer surface of the trigger lip 62 gradually extends from the body of the trigger 28 at an angle, while the inner surface of the trigger lip 62 is substantially perpendicular to the body of the trigger 28.

As the trigger 28 moves from the de-activated position to the activated position, the outer surface of the trigger lip 62 comes in contact with the outer surface of the pivot catch lip 60. As the outer surfaces of both the trigger lip 62 and the pivot catch lip 60 are curved or gradually extend from their respective bodies, the outer surface of the trigger lip 62 slides across the outer surface of the pivot catch lip 60. Once across the outer surface of the pivot catch lip 60, the inner surface of the trigger lip 62 engages with the inner surface of the pivot catch lip 60, and rests substantially against the entire inner surface of the pivot catch lip 60. As the inner surfaces of the pivot catch lip 60 and the trigger lip 62 are substantially parallel to one another, the inner surfaces do not slide against one another in the horizontal direction, thereby holding the trigger 28 in the activated position.

In the illustrated embodiment, the shortening of the nitinol wire 52 causes the pivot catch 48 to rotate in the direction of the nitinol wire 52. The rotation of the pivot catch 48 causes the inner surface of the pivot catch lip 60 to slide along the inner surface of the trigger lip 62 and in the direction of the nitinol wire 52, thereby disengaging the pivot catch 48 from the trigger 28, as the pivot catch 48 is no longer in contact with the trigger 28. The tension in the trigger spring 54 returns the trigger 28 to the de-activated position.

Figure 13:
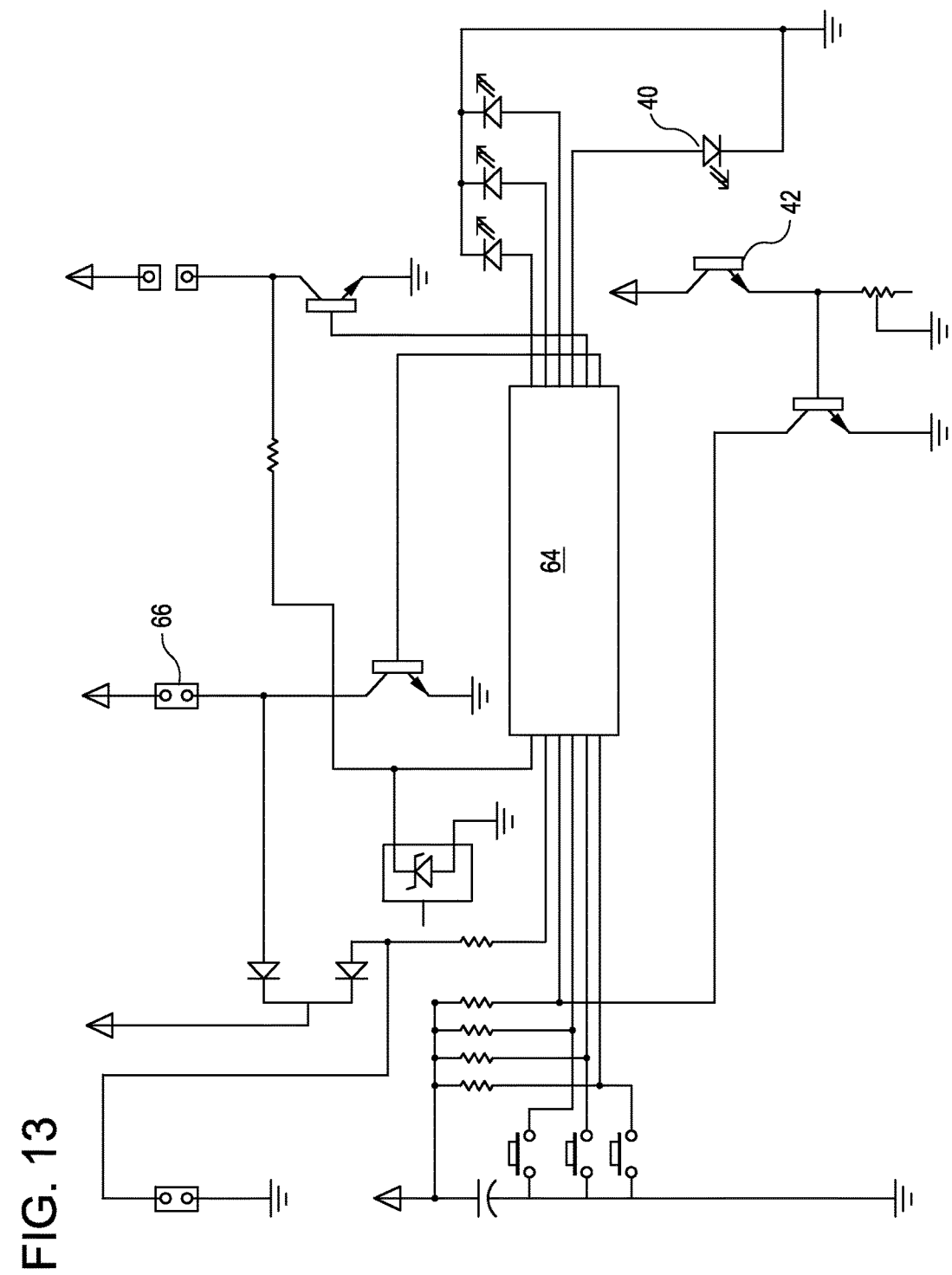
FIG. 13 is an example circuit diagram describing the connections between components on a printed circuit board, according to one embodiment.

FIG. 13 is an example circuit diagram describing the connections between components on the printed circuit board 24 and other components of the device 10. In the illustrated components include a microcontroller 64 disposed on the printed circuit board 24, a speaker connection 66, the light sensor 42, and the optical transmitter 40. In the illustrated embodiment, the microcontroller 64 receives a signal from the light sensor 42 indicative of the intensity of light measured by the light sensor 42. Based on the signal received from the light sensor 42, the microcontroller 64 determines if an alarm event should be triggered. For example, when the value associated with the signal received from the light sensor 42 drops below a specified value, the microcontroller triggers an alarm event. In the illustrated embodiment, the microcontroller 64 sends a signal to the speaker connection 66, causing a speaker connected to the speaker connection 66 to sound an audible alarm for a period of time, when an alarm event is triggered. The audible alarm helps notify the practitioner that the level of fluid in the drip chamber 16 has dropped below a predetermined level and the fluid supply reservoir 14 is dry or is on the verge of running dry. In the illustrated embodiment, the microcontroller 64 sends the optical transmitter 40 a signal causing the optical transmitter to continuously transmit light.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure. For example, the device 10 can be adapted to attach to chambers of various sizes, such as larger chambers used for continuous bladder irrigation fluid delivery, and smaller chambers used for fluid delivery in pediatric population. Additionally, the device 10 can be adapted to allow use with non-vertically oriented flexible fluid delivery tubes with the sensor alignment being modified or adjustable as suitable. As yet another example, the device 10 can be made from snap together components, thereby avoiding the need for any visible fasteners.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

What is claimed is:

1. A method for monitoring and/or controlling delivery of a fluid to a patient through a flexible fluid delivery tube, the method comprising:
   providing a fluid-flow monitoring and/or control device removeably mountable to a fluid delivery system configured to deliver the fluid to the patient, the fluid delivery system including the flexible fluid delivery tube, the fluid-flow control device including a fluid level sensing mechanism;
   using the fluid level sensing mechanism to detect that a fluid level of the fluid supplied through the flexible delivery tube has dropped below a predetermined level; and
   in response to the detection of the fluid level dropping below the predetermined level:
      generating an alarm indicating that the fluid level has dropped below the predetermined level; and
      reconfiguring a flow control mechanism from a first configuration in which flow of the fluid through the fluid delivery system is not blocked to a second configuration in which the flow of the fluid through the fluid delivery system is blocked by a portion of the flow control mechanism that is moved to interface with the fluid delivery system by:
         configuring a trigger that is operatively coupled with the flow control mechanism in an actuated configuration in which the flow control mechanism is in the first configuration;
         engaging a latching mechanism with a trigger to retain the trigger in the actuated configuration prior to the detection of the fluid level dropping below the predetermined level; and induceing a length change in a shape memory wire that is operatively coupled with the latching mechanism so as to disengage the latching mechanism from the trigger and move the trigger from the actuated configuration to a non-actuated configuration which reconfigures the flow control mechanism from the first configuration to the second configuration in response to the detection of the fluid level dropping below the predetermined level.

2. The method of claim 1, comprising interfacing the flow control mechanism with an exterior surface of the flexible delivery tube to deform the flexible delivery tube to block flow of fluid through the flexible delivery tube when the flow control mechanism is reconfigured from the first configuration to the second configuration.

3. The method of claim 2, wherein reconfiguring the flow control mechanism from the first configuration to the second configuration comprises reorienting an interface surface of the flow control mechanism from a first position and/or orientation to a second position and/or orientation in which the interface surface interfaces with the flexible delivery tube.

4. The method of claim 3, wherein reconfiguring the flow control mechanism from the first configuration to the second configuration comprises rotating a rotatable shaft having the interface surface as an external surface of a non-cylindrical length of the rotatable shaft.

5. The method of claim 1, comprising biasing the trigger towards the non-actuated configuration with a spring mechanism operatively coupled with the trigger.

6. The method of claim 5, wherein the fluid level sensing mechanism transmits a light beam through the flexible delivery tube or a drip chamber fluidly coupled with the flexible delivery tube and outputs a signal from a light sensor indicative of whether the fluid level is above or below the predetermined level, the method comprising:

monitoring the signal output from the light sensor with a control circuit configured to detect when the fluid level drops below the predetermined level; and upon the control circuit detecting when the fluid level drops below the predetermined level, outputting a control signal from the control circuit that induces disengagement of the latching mechanism from the trigger.

7. The method of claim 1, comprising delivering an intravenous fluid, a medication fluid, an intravenous nutritional fluid, a blood plasma fluid, a bladder irrigation fluid, a fluid to a pediatric patient, a fluid during an interventional radiology procedure with pressurized arterial delivery, or a pressurized intravenous fluid to the patient via the flexible fluid delivery tube.

8. A device for monitoring and controlling delivery of a fluid to a patient through a flexible fluid delivery tube, the device comprising:

a fluid level sensing mechanism configured to detect that a fluid level of the fluid supplied by the flexible fluid delivery tube has dropped below a predetermined level;

a flow control mechanism that is operatively coupled with the fluid sensing mechanism and configured to, in response to the detection of the fluid level dropping below the predetermined level, reconfigure from a first configuration in which flow of the fluid through the flexible delivery tube is not blocked so as to enable delivery of the fluid to the patient to a second configuration in which the flow control mechanism interfaces with the flexible delivery tube to block flow of the fluid through the flexible delivery tube;

a trigger that is operatively coupled with the flow control mechanism and is reconfigurable from an actuated configuration in which the flow control mechanism is in the first configuration to a non-actuated configuration in which the flow control mechanism is in the second configuration;

a latching mechanism that is configured to be engaged with the trigger to retain the trigger in the actuated configuration prior to the detection of the fluid level dropping below the predetermined level; and a shape memory wire that is operatively coupled with the latching mechanism to disengage the latching mechanism from the trigger allowing the trigger to move to the non-actuated configuration and reconfigure the flow control mechanism from the first configuration to the second configuration when the shape memory wire undergoes a length change in response to the detection of the fluid level dropping below the predetermined level, wherein the device is removeably mountable to a fluid delivery system configured to deliver the fluid to the patient, the fluid delivery system including the flexible fluid delivery tube, and the device generates an alarm and blocks flow of the fluid through the flexible fluid delivery tube in response to detecting that the fluid level has dropped below the predetermined level.

9. The device of claim 8, wherein the device is removeably mountable to the flexible fluid delivery tube.

10. The device of claim 8, wherein the fluid sensing mechanism comprises a light transmitter and a light sensor, the light transmitter being configured to transmit a beam of light through the flexible delivery tube or a drip chamber fluidly coupled with the flexible delivery tube, the light sensor being configured to output a signal indicative of an amount of the light beam incident on the light sensor, the amount of light incident being indicative of whether the fluid level is above or below the predetermined level.

11. The device of claim 8, comprising a control circuit configured to, in response to detecting when the fluid level drops below the predetermined level, output a control signal that induces reconfiguration of the flow control mechanism from the first configuration to the second configuration.

12. The device of claim 8, wherein the flow control mechanism, when reconfigured from the first configuration to the second configuration, deforms the flexible deliver tube to block flow of the fluid through the flexible delivery tube.

13. The device of claim 12, wherein the flow control mechanism comprises an interface surface reconfigurable from a first position and/or orientation to a second position and/or orientation in which the interface surface interfaces with the flexible delivery tube.

14. The device of claim 13, wherein the interface surface is an external surface of a non-cylindrical length of a rotatable shaft that is rotated during reconfiguration of the flow control mechanism from the first configuration to the second configuration.

15. The device of claim 8, wherein the trigger is operatively coupled with a spring mechanism configured to bias the trigger towards the non-actuated configuration.

16. The device of claim 15, wherein the fluid level sensing mechanism transmits a light beam through the flexible delivery tube or a drip chamber fluidly coupled with the flexible delivery tube and outputs a signal from a light sensor indicative of whether the fluid level is above or below the predetermined level, the device comprising a control circuit that monitors the signal output from the light sensor to detect when the fluid level drops below the predetermined level and outputs a control signal that induces disengagement of the latching mechanism from the trigger upon detecting when the fluid level drops below the predetermined level.

17. The device of claim 16, wherein the control signal output from the control circuit induces the length change in the shape memory wire.

18. The device of claim 8, wherein the fluid supplied to the patient is an intravenous fluid, a medication fluid, an intravenous nutritional fluid, a blood plasma fluid, or a bladder irrigation fluid.

* * * * *